US00PP16930P2

(12) United States Plant Patent
Crowther

(10) Patent No.: US PP16,930 P2
(45) Date of Patent: Aug. 1, 2006

(54) ***EUPHORBIA* PLANT NAMED 'WALEUTINY'**

(50) Latin Name: *Euphorbia martinii*
Varietal Denomination: Waleutiny

(76) Inventor: Albert Timothy Crowther, Walberton Nursery, Yapton Lane, Walberton, Arundel (GB), BN180AS ( * ) Notice: Subject to any disclaimer, the term of this patent is extended or adjusted under 35 U.S.C. 154(b) by 97 days.

(21) Appl. No.: 10/836,138

(22) Filed: May 3, 2004

(51) Int. Cl.
*A01H 5/00* (2006.01)

(52) U.S. Cl. ..... Plt./302

(58) Field of Classification Search ..... Plt./302
See application file for complete search history.

*Primary Examiner*—Kent Bell
*Assistant Examiner*—Louanne Krawczewicz Myers

(57) ABSTRACT

A new cultivar of *Euphorbia* named 'Waleutiny' that is distinguished by dwarf size, compact habit, burgundy and green stems, small burgundy and green leaves and lime-green flowers. In combination these traits set 'Waleutiny' apart from all other existing varieties of *Euphorbia* known to the inventor.

2 Drawing Sheets

Genus: *Euphorbia.*
Species: *martinii.*
Denomination: Waleutiny.

BACKGROUND OF THE INVENTION

The present invention relates to a new and distinct cultivar of spurge, an ornamental plant that is suitable for use in container, rock garden, or as a groundcover in the landscape. The new invention is known botanically as *Euphorbia martinii,* and will be referred to hereinafter by the cultivar name 'Waleutiny'.

In December 2000 'Waleutiny' was selected by the inventor, in a cultivated area of Walberton, West Sussex, United Kingdom. The parent is an individual unnamed selection of *Euphorbia martinii* (unpatented). 'Waleutiny' was discovered at the inventor's nursery as a naturally occurring single branch sport on an individual *Euphorbia martinii* that was growing in a commercial crop of *Euphorbia martinii.* 'Waleutiny' is distinguishable from the parent plant by overall size. *Euphorbia martinii* is generally described as growing to a height of 60 cm or to a height within the range 45 cm to 75 cm; and a spread of 45 cm to 60 cm. 'Waleutiny' achieves a height of approximately 30 cm and ranges in width from 15 cm to 30 cm. When compared with the parent, the leaves and the inflorescence (cyathia) of 'Waleutiny' are smaller and in proportion to the parent. In overall appearance, 'Waleutiny' resembles a miniature version of the parent *Euphorbia martinii.*

The first asexual reproduction of 'Waleutiny' was conducted in 2001 by the inventor in a cultivated area of West Sussex within the United Kingdom. The method used for propagation was direct rooting of the excised branch as discovered. Since then the new cultivar named 'Waleutiny' has been further asexually propagated by tip and branch cuttings, has been determined stable, firmly fixed, and reproduces true to type in successive generations.

SUMMARY OF THE INVENTION

The following traits have been repeatedly observed and represent the distinguishing characteristics of the new

*Euphorbia* cultivar named 'Waleutiny'. These traits in combination distinguish 'Waleutiny' from all other existing varieties of *Euphorbia* known to the inventor. 'Waleutiny' has not been tested under all possible conditions and phenotypic differences may be observed with variations in environmental, climatic, and cultural conditions, however, without any variance in genotype.

1. *Euphorbia martinii* 'Waleutiny' exhibits compact habit.
2. *Euphorbia martinii* 'Waleutiny' exhibits small lime-green flowers in spring and summer.
3. *Euphorbia martinii* 'Waleutiny' exhibits small leaves that are green and burgundy in color.
4. *Euphorbia martinii* 'Waleutiny' exhibits green and burgundy stems.
5. *Euphorbia martinii* 'Waleutiny' is propagated using the method of vegetative tip and branch cuttings.
6. *Euphorbia martinii* 'Waleutiny' is hardy to USDA Zone 7.
7. *Euphorbia martinii* 'Waleutiny' is 15 cm to 30 cm in width, 30 cm. in height at the top of the flowers, and 15 cm. in height at the top of the foliage.
8. *Euphorbia martinii* 'Waleutiny' is suitable for use in container, rock garden, and as a groundcover in the landscape.

BRIEF DESCRIPTION OF THE DRAWINGS

The accompanying color drawings

Figure 1:
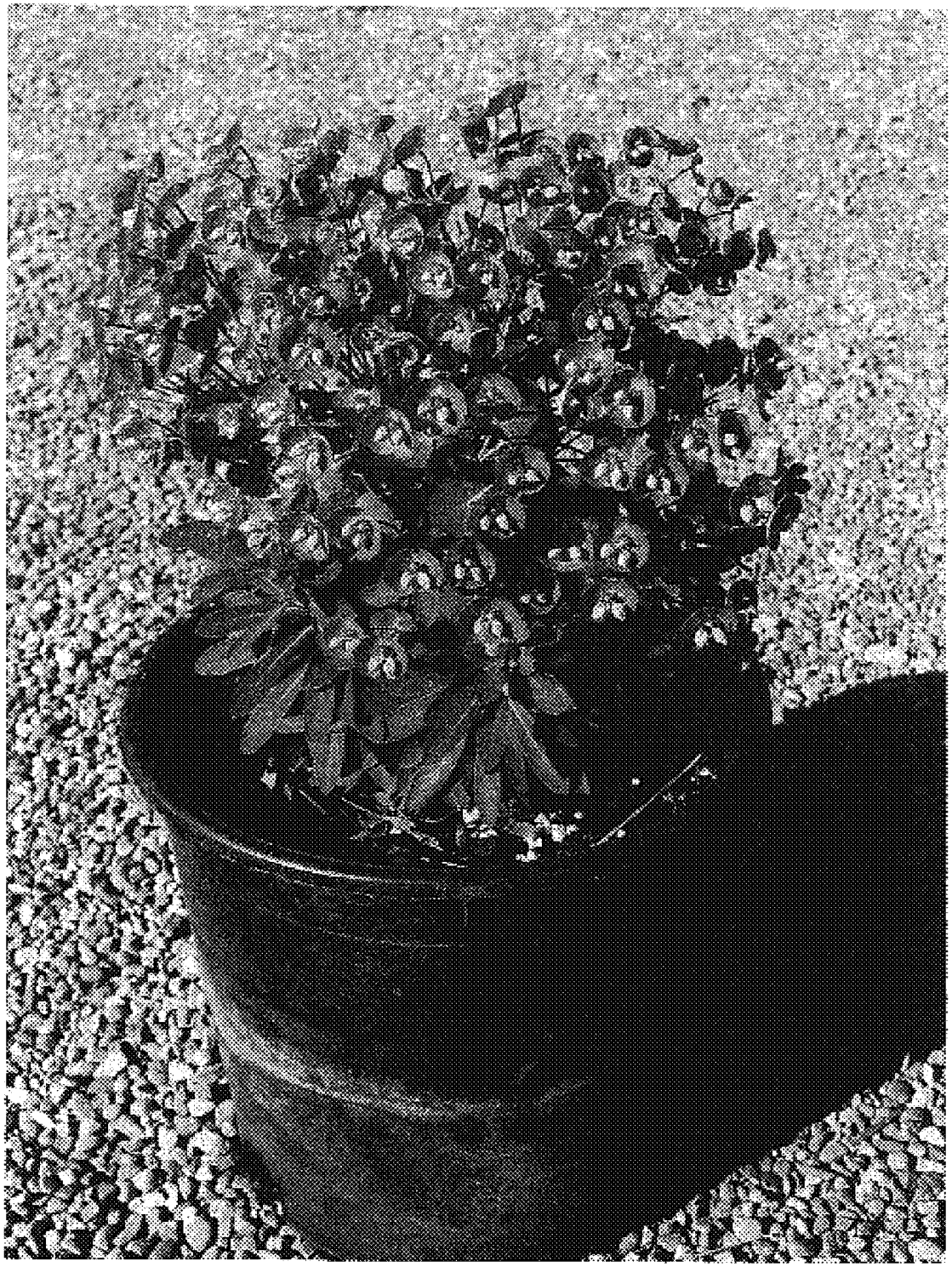
FIG. 1 and FIG. 2 illustrate the overall appearance of the new *Euphorbia* cultivar 'Waleutiny' showing the colors as true as it is reasonably possible to obtain in colored reproductions of this type. Colors in the photograph may differ from the color values cited in the detailed botanical description, which accurately describe the actual colors of the new variety 'Waleutiny'.

The drawing labeled as FIG. 1 illustrates the entire plant in bloom from a side perspective.

Figure 2:
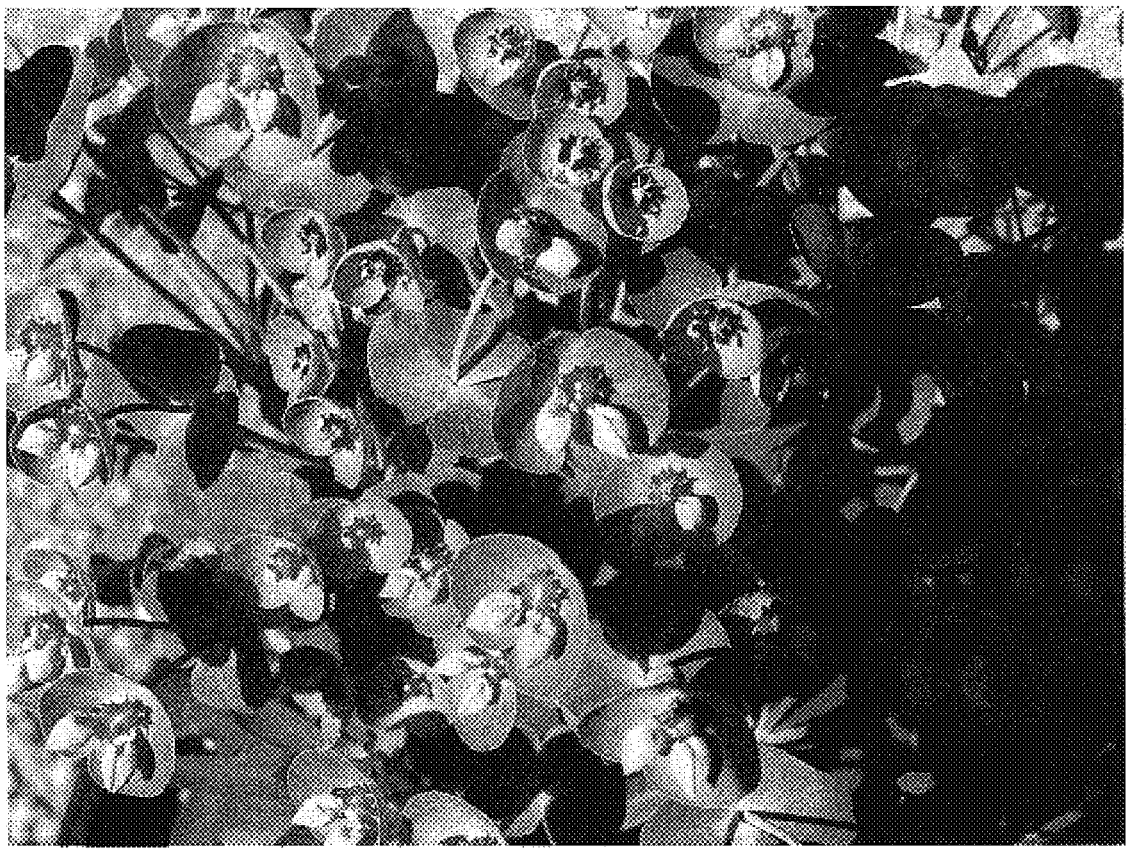

The drawing labeled as FIG. 2 illustrates a close-up view of the inflorescence (cyathium).

The drawings were made were made using conventional techniques and although flower and foliage colors may appear different from actual colors due to light reflectance, they are as accurate as possible by conventional photography.

BOTANICAL DESCRIPTION OF THE PLANT

The following is a detailed botanical description of the new *Euphorbia* cultivar 'Waleutiny'. Observations, measurements, values and comparisons were collected in Arroyo Grande, Calif. from 2-liter container plants that were 12-months-old at the time and grown out-of-doors in full sun. Color determinations are made in accordance with the 2001 edition of The Royal Horticultural Society Colour Chart of London, England, except where general color terms of ordinary dictionary significance are used. The growing requirements of the new variety are similar to the species.

Botanical classification: *Euphorbia martinii* 'Waleutiny'.
Genus: *Euphorbia.*
Species: *martinii.*
Denomination: Waleutiny.
Common name: Spurge.
Commercial classification: Sub-shrub.
Size: Dwarf.
Parentage: *Euphorbia* 'Waleutiny' is a naturally occurring single branch sport discovered on an individual plant of the following parent: *Euphorbia martinii* (unpatented).
Asexual propagation method: Vegetative tip and branch cuttings.
Rooting habit: Fine.
Time to develop roots: 2 weeks are needed for roots to develop on an initial cutting.
Temperature recommended to develop roots: 18° Centigrade.
Crop time: 8 months are needed to produce a finished 1-liter container from a rooted cutting.
Growth habit: Compact habit.
Plant shape: Ball-shaped.
Use: Ornamental plant suitable for use in container, rock garden, and as a groundcover for the landscape.
Type: Perennial.
Vigor: Moderate vigor.
Height of plant (after one season): 15 cm. in height at the top of the foliage and 30 cm. in height at the top of the flowers.
Width of plant (after one season): 15 cm to 30 cm in width.
Cultural requirements: Sun or partial shade and well-draining soil.
Diseases and pests: Can be affected by mildew or rust diseases.
Hardiness: Hardy USDA Zone 7.
Special considerations: Hazardous. All parts exude a white milky substance when bruised that can be toxic and may elicit dermal irritation.
Stem:
- *Branching habit.*—Central trunk with many branching stems.
- *Trunk dimensions.*—3 cm. in diameter and 3 cm. in height.
- *Trunk shape.*—Cylindrical to columnar.
- *Trunk surface.*—Pubescent surface.
- *Trunk color.*—Individual colors 183A and 144B are present on an individual trunk.
- *Lateral stem color.*—Individual colors 183A and 144B are present on an individual lateral stem.
- *Lateral stem shape.*—Cylindrical to columnar.
- *Lateral stem diameter.*—0.50 cm. in diameter.
- *Lateral stem length.*—Lateral stem ranges from 12 cm. to 15 cm. in length.
- *Lateral stem surface.*—Pubescent.
- *Internode length.*—Internodes are 3 mm. in length.

Foliage:
- *Type: Evergreen.*
- *Leaf arrangement.*—Spirally arranged.
- *Leaf division.*—Simple.
- *Leaf shape.*—Oblanceolate.
- *Leaf length.*—Individual leaf ranges from 4 cm. to 6 cm. in length on an individual plant.
- *Leaf width.*—Individual leaf ranges from 0.50 cm. to 1 cm. in width on an individual plant.
- *Leaf apex.*—Apiculate.
- *Leaf base.*—Attenuate.
- *Quantity of leaves.*—A range of 65–75 leaves per stem.
- *Leaf venation pattern (abaxial and adaxial surfaces).*—Pinnate with only the mid-vein prominent.
- *Vein color (abaxial surface).*—139D.
- *Vein color (adaxial surface).*—139D.
- *Margin.*—Entire.
- *Leaf surface (abaxial surface).*—Pubescent.
- *Leaf surface (adaxial surface).*—Pubescent.
- *Leaf appearance (adaxial and abaxial surfaces).*—Matte.
- *Leaf attachment.*—Sessile.
- *Leaf color (adaxial surface).*—Individual colors 139A and 183A are present on an individual leaf.
- *Leaf color (abaxial surface).*—Individual colors 137B and 183A are present on an individual leaf.
- *Leaf fragrance.*—None observed.

Inflorescence:
- *Type.*—Consists of 20–30 cyathia arranged in pairs and borne on a pedicel which divides at a basally fused perfoliate subtending bracts.
- *Blooming season.*—Spring and summer.
- *Hardiness (including buds).*—Minor frost damage to USDA Zone 7, severe in zones colder than USDA Zone 7.
- *Dimensions of inflorescence.*—15 cm. in diameter and 10 cm. in depth.
- *Dimensions of individual cyathium.*—Cyathium is 0.75 cm. in depth and ranges from 1 cm. to 1.25 cm. in diameter.
- *Cyathium arrangement.*—Whorled.
- *Cyathium shape.*—Cupulate.
- *Cyathium apex.*—Rounded.
- *Cyathium base.*—Fused.
- *Cyathium margin.*—Entire.
- *Color of cyathia (both adaxial and abaxial surfaces).*—147B and 183D.
- *Aspect.*—Facing upward and outward.
- *Bud shape.*—Oval in shape.
- *Bud dimensions.*—4 mm. in length and 3 mm. in diameter.
- *Bud surface.*—Glabrous.
- *Bud color.*—N144A.
- *Bud apex.*—Acute.

Inflorescence peduncle:
- *Dimensions.*—Peduncle is 9 cm. in length and 4 mm. in diameter.

*Peduncle color.*—Colors 144B and 183A are individually present on an individual peduncle.
*Peduncle shape.*—Cylindrical in shape.
*Peduncle appearance.*—Semi-glossy.
*Peduncle surface.*—Mostly glabrous but with a few hairs.
*Pedicel length.*—Pedicel ranges from 3 mm. to 2.25 cm. in length (upper third divides at perfoliate subtending bracts).
*Pedicel diameter.*—Pedicel is 2 mm. in diameter below bract and 1 mm. in diameter above bract.
*Pedicel color.*—144B.
*Pedicel texture.*—Soft and flexible.
*Pedicel shape.*—Cylindrical in shape.
*Pedicel surface.*—Puberulent surface.
*True perianth.*—Absent.
*Number of subtending bracts.*—2 subtending bracts per pedicel.
*Subtending bracts fused or unfused.*—Subtending bracts are basally fused.
*Subtending bract color* (*abaxial surface*).—Colors 147B and 183D are individually present on subtending bract.
*Subtending bract color* (*adaxial surface*).—Colors 147B and 183D are individually present on subtending bract.
*Subtending bract margin.*—Entire.
*Subtending bract shape.*—Closest to reniform in shape.
*Subtending bract apex.*—Obtuse apex.
*Subtending bract base.*—Closest to truncate.
*Subtending bract dimensions.*—0.75 cm. in length and 1 cm. in width.
*Subtending bract surfaces* (*adaxial and abaxial surfaces*).—Glabrous.
*Subtending bract attachment.*—Perfoliate.
*Lastingness of cyathium on plant.*—An individual cyathium lasts from 10 to 15 days on an individual plant.
*Lastingness of cyathium* (*when removed from plant*).—Cyathium lasts an average of 24 hours when removed from plant.
*Cyathium fragrance.*—None observed.

Reproductive organs:
*Stamen color.*—144D.
*Number of stamens.*—Four in number.
*Stamen dimensions.*—2 mm. in length and 0.25 mm. in diameter.
*Anther dimensions.*—0.50 mm. in length and 0.25 mm. in width.
*Anther shape.*—Bifid.
*Pollen color.*—1B.
*Quantity of pollen.*—Low amount of pollen.
*Nectaries.*—4 in number.
*Nectary surface.*—Glabrous.
*Nectary appearance.*—Glossy.
*Nectary color.*—Colors N144A and 183A are individually present on an individual nectary.
*Nectary dimensions.*—3 mm. in width and 1.25 mm. in length.
*Nectary shape.*—Concavo-convex in shape.
*Pistil.*—One in number.
*Pistil dimensions.*—3 mm in length, 1 mm in width.
*Pistil color.*—144A.
*Style number.*—3 styles in number joined at their bases.
*Style dimensions.*—1 mm. in length and 0.1 mm in width.
*Style color.*—N144A.
*Stigma color.*—N144D.
*Stigma number and shape.*—3 stigmas in number and each individual stigma bi-fid in shape.
*Stigma dimensions.*—0.50 mm. in length and 0.1 mm in width.
*Ovary shape.*—A combination of globular and trilocular in shape.
*Ovary surface.*—Pubescent.
*Ovary dimensions.*—1.50 mm. in width and 1.50 mm. in height.
*Ovary color.*—144A.
*Ovary position.*—Superior.

Seed: No seed has been observed to date.

It is claimed:

1. A new and distinct cultivar of *Euphorbia* plant named 'Waleutiny' as described and illustrated.

* * * * *